United States Patent
Verrelst et al.

(12) 
(10) Patent No.: US 6,300,536 B1
(45) Date of Patent: Oct. 9, 2001

(54) CATALYST HAVING A ZEOLITIC CORE AND ZEOLITIC LAYER AND THE USE OF THE CATALYST FOR OLEFIN OLIGOMERIZATION

(75) Inventors: Wim Herman Verrelst, Edegem; Luc Roger Marc Martens, Meise; Johannes Petrus Verduijn, Leefdaal, all of (BE)

(73) Assignee: Exxon Mobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/436,485

(22) Filed: Nov. 8, 1999

Related U.S. Application Data

(63) Continuation of application No. 08/875,749, filed on Oct. 27, 1997, now Pat. No. 6,013,851.

(30) Foreign Application Priority Data

Feb. 7, 1995 (GB) .................................................. 9502342

(51) Int. Cl.⁷ ............................... C07C 2/02; B01J 24/06; B01J 21/00
(52) U.S. Cl. ............................... 585/533; 502/67; 502/71; 502/77
(58) Field of Search ............................... 585/533; 502/67, 502/71, 77

(56) References Cited

U.S. PATENT DOCUMENTS

| | | | |
|---|---|---|---|
| 4,203,869 | 5/1980 | Rollmann | 252/455 Z |
| 4,394,362 | 7/1983 | Miller | 423/328 |
| 4,788,374 | 11/1988 | Chu et al. | 585/533 |
| 4,847,224 | 7/1989 | Fajula et al. | 502/67 |
| 4,975,401 | 12/1990 | Kaeding et al. | 502/67 |
| 5,177,282 | 1/1993 | Nierlich et al. | 585/329 |
| 5,250,484 | 10/1993 | Beck et al. | 502/71 |
| 5,278,114 | 1/1994 | Wielers et al. | 502/67 |
| 5,284,989 | 2/1994 | Apelian et al. | 585/533 |
| 5,292,696 | 3/1994 | Ito et al. | 502/66 |

FOREIGN PATENT DOCUMENTS

| | | | |
|---|---|---|---|
| 118632 | * | 3/1983 | (EP) . |
| 0169025 | | 1/1986 | (EP) . |
| 0311310 | | 4/1989 | (EP) . |
| 9325475 | | 12/1993 | (WO) . |
| 9425151 | | 11/1994 | (WO) . |
| 9522516 | | 8/1995 | (WO) . |

* cited by examiner

*Primary Examiner*—Hien Tran
*Assistant Examiner*—Thuan D. Dang

(57) ABSTRACT

A molecular sieve comprising a core having deposited thereon a surface layer, wherein the core is a zeolite containing silicon and at least one element selected from gallium and iron and the surface layer has a higher Si:Al ratio than that of the silicon:selected element ratio of the core, provides for lower branching in olefin oligomerization products.

14 Claims, No Drawings

CATALYST HAVING A ZEOLITIC CORE AND ZEOLITIC LAYER AND THE USE OF THE CATALYST FOR OLEFIN OLIGOMERIZATION

This application is a continuation of application Ser. No. 08/875,749, filed Oct. 27, 1997 now U.S. Pat. No. 6,013,851.

FIELD OF THE INVENTION

This invention relates to the treatment of hydro-carbons, especially olefinic hydrocarbons, to effect oligomerization, and to catalysts for use in such treatment.

BACDGROUND OF THE INVENTION

Olefinic hydrocarbons are employed as starting materials in the hydroformylation, or oxo, process, for the eventual manufacture of numerous valuable products, e.g., alcohols, esters and ethers derived therefrom, aldehydes, and acids. In many of these end uses, linear or lightly branched hydrocarbon chains have advantages compared with more heavily branched chains.

In the oxo process itself, moreover, olefins with heavily branched chains are less reactive than those with linear or lightly branched structures and, for a given degree of branching, certain isomers are less reactive than others.

Olefinic feedstocks, especially in the $C_4$ to $C_{20}$, and more particularly in the $C_6$ to $C_{15}$ range, are frequently produced by oligomerization of lower molecular weight original starting materials, a process that, because of rearrangements that take place during the reaction, may produce an undesirably high proportion of multiply branched olefins, even if the original materials are linear. Also, the locations of the branches, at sites close to each other on the hydrocarbon chain, or in the central region of the chain, or both, resulting from the oligomerization further reduce the reactivity of the molecules in the oxo reaction.

There are other areas in which a less highly branched hydrocarbon has advantages; these include the alkylation of aromatic hydrocarbons by reaction with olefins in the manufacture of surfactants and polyolefin stabilizers.

There is accordingly a need to provide a method to produce an olefin oligomer having a reduced degree of branching of a hydrocarbon material.

U.S. Pat. No. 5,284,989 (Apelian, et al, assigned to Mobil Oil Corporation) describes the use of a medium pore size shape-selective acid crystalline zeolite in the catalytic oligomerization of olefinic hydrocarbons, and discusses the factors influencing the linearity or degree of branching of the products. Acid activity at the zeolite particle surface is said to favour the production of branched products, and reference is made to dealumination of zeolite surfaces to reduce surface acidity, or the ratio of surface acidity to intracrystalline acid site activity. Other reduction methods mentioned in an extensive prior art review in the patent include the use of bulky amines to inactivate acid sites; the invention to which the patent is directed is the use of a dicarboxylic acid to inactivate the surface acid sites.

In U.S. Pat. No. 5,250,484 (Beck et al., also assigned to Mobil), surface acidity is reduced by contacting the catalyst with an ammonia-borane solution and calcining to form an inactive ceramic layer on the surface. In U.S. Pat. No. 4,788,374 (Chu et al;., also assigned to Mobil), surface acidity is reduced by forming a silica shell on a metallosilicate core by crystallizing silica on the surface of the core in the presence of fluoride.

SUMMARY OF THE INVENTION

The present invention provides a process for the oligomerization of an olefin, which comprises contacting under oligomerization conditions a feed comprising at least one olefin with an olefin oligomerization catalyst comprising a particulate molecular sieve, each particle of the molecular sieve comprising a core having deposited thereon a surface layer, the core comprising a zeolite containing silicon and at least one element selected from aluminium, gallium and iron, and the surface layer comprising a zeolite containing silicon and at least one element selected from aluminium, gallium and iron, the zeolite of the surface layer being of the same crystalline structure as the core and having a higher silicon:selected element ratio than that of the core.

The invention also provides a particulate molecular sieve, capable of catalysing olefin oligomerization, each particle of the molecular sieve comprising a core having deposited thereon a surface layer, the core comprising a zeolite containing silicon and at least one element selected from aluminium, gallium and iron, and the surface layer comprising a zeolite containing silicon and at least one element selected from aluminium, gallium and iron, the zeolite of the surface layer being of the same crystalline structure as the core and having a higher silicon:selected element ratio than that of the core.

The invention further provides the use of a particulate molecular sieve, each particle of the molecular sieve comprising a core having deposited thereon a surface layer, the core comprising a zeolite containing silicon and at least one element selected from aluminium, gallium and iron, and the surface layer comprising a zeolite containing silicon and at least one element selected from aluminium, gallium and iron, the zeolite of the surface layer being of the same crystalline structure as the core and having a higher silicon-:selected element ratio than that of the core, as an olefin oligomerization catalyst to reduce the degree of branching of the oligomer product.

The invention still further provides a process for the manufacture of a particulate molecular sieve, which comprises heating an aqueous synthesis mixture comprising a source of silicon, a source of an element selected from aluminium, gallium and iron, a source of monovalent inorganic cations, and, if desired or required, an organic structure directing agent, the synthesis mixture having dispersed therein crystals of a molecular sieve containing silicon and an element selected from aluminium, gallium, and iron, the molar ratio of silicon to selected element in the crystals being lower than the molar ratio of silicon to selected element in their respective sources in the synthesis mixture, to cause crystallization of a molecular sieve layer from the synthesis mixture onto the surfaces of the crystals.

DETAILED DESCRIPTION OF THE INVENTION

In each of the above-mentioned aspects of the invention, the selected element is advantageously aluminium. The elements selected for the core and for the outer layer are advantageously, but not necessarily, the same. For example, a gallium-containing outer layer may surround an aluminium-containing core.

Advantageously, the resulting crystalline product is ion exchanged with ammonium ions or protons, and calcined to yield the acid form of the molecular sieve. Advantageously, calcination takes place at a temperature of at most 600° C., preferably at most 500° C.

Certain features of the process for the manufacture of the molecular sieve of the present invention are shared with processes known in the art as commonly practised or as described in the literature.

These may be described briefly, as follows:

| | |
|---|---|
| Propene | up to 50% |
| Propane | up to 10% |
| $C_4^+$ | up to 95% |
| Polyunsaturates | up to 1.5% |

(As used herein, the term polyunsaturates includes compounds having two or more unsaturated carbon to carbon bonds, whether double or triple, and also compounds other than acetylene which contain one triple bond, e.g., propyne.)

Higher boiling components, especially $C_5^+$ hydrocarbons, may be removed from such a feedstream source as a desirable product, e.g., naphtha from fluid bed catalytic cracking, as a result of processing or to avoid further handling of by-products. For example, the tar formed from steam cracking of vacuum gas oil may be removed as an undesirable by-product in the primary fractionation of the process gas, while the $C_5^+$ component of the product from steam cracking of ethane may be removed during the quench and process gas compression stages immediately following cracking.

Intermediate boiling components ($C_3^+$) of a feedstream source may also be removed from the dilute olefin stream as a desired co-product or to avoid further handling of by-products. For example, propene may be removed from the process gas effluent of cracked naphtha for use as a chemical feedstock. production of the crystalline framework the organic compound acts as a template around which the crystalline framework grows, or which causes the crystallization to be directed to form a particular crystalline framework. Preferred agents for the manufacture of ZSM-22 sieves are mono- and di-aminoalkanes having up to 12 carbon atoms, particularly 4, 6, 8, 10 or 12 carbon atoms, e.g. 1,6-diaminohexane (which is preferred), diethylamine, 1-aminobutane or 2,2'-diaminodiethylamine; arylamines containing up to 8 carbon atoms, heterocyclic organic compounds, e.g., as N-ethylpyridinium; poly-alkylenepolyamines, e.g. triethylene tetramine or tetraethylene pentamine, and alkanolamines, e.g. ethanolamine or diethanolamine.

A preferred quantity of template R, based on the preferred template of 1,6-diaminohexane, is a molar ratio of $R/SiO_2$ in the synthesis mixture of 0.025 to 0.4.

The $SiO_2/Al_2O_3$ molar ratio in the synthesis mixture is generally at least 150:1, preferably at least 250:1, and may be as high as 1500:1. Ratios between 300:1 and 900:1, especially between 300:1 and 600:1, are especially preferred.

The $SiO_2/Al_2O_3$ molar ratio in the zeolite layer after crystallization may be up to 30% lower than the molar ratio in the synthesis mixture; this reduction may be taken into account in selecting the proportions of components in the synthesis mixture, to ensure the required relationship between core and outer layer ratios. The $SiO_2/Al_2O_3$ molar ratio in the core crystals dispersed in the synthesis mixture is advantageously at most 120:1, is more advantageously in the range 40:1 to 120:1, and preferably in the range 60 to 100:1.

The proportions of reactants in the synthesis mixture are generally lower than in the normal synthesis mixture, i.e., in addition to the lower aluminium content, the synthesis mixture should be highly diluted, for example, with water. The synthesis mixture including the core material may contain, for example, up to 85%, advantageously from 50 to 80% by weight, of diluent, especially water.

Advantageously, crystallization is effected at 120 to 180° C., preferably 140 to 170° C. The crystallization time may be from 10 to 72 hours, typically 15 to 48 hours.

After crystallization the zeolite may be washed with deionized water or with acidified water, and then, optionally after a drying or calcining step, ion exchanged to yield the acidic form.

The zeolite is preferably exchanged with ammonium ions and subjected to conditions under which the ammonium ions decompose, with the formation of ammonia and a proton, thus producing the acidic form of the zeolite. Alternatively the acid form may be obtained by acid exchange with, for example, hydrochloric acid.

The exchange with ammonium ions may be carried out by any suitable method, for example, by treating the crystals with an aqueous solution of ammonium chloride, ammonium nitrate or ammonium hydroxide. Exchange with protons is advantageously carried out by contacting the crystals with a dilute acid solution, e.g., HCl.

After exchange with ammonium ions or protons, the crystals may be calcined, advantageously at a temperature of from 120° to 600° C., preferably from 150° to 500° C. Suitable calcination times range from 1 hour to several days, the temperatures in the upper part of the specified temperature range corresponding to the shorter heating times and the temperatures in the lower part of the specified temperature range corresponding to the longer heating times.

Thus, for example, crystals may be calcined at a temperature of 400° C. for from 1 to 20 hours. At a temperature of 120° C., longer calcination times of at least 2 days and preferably from 3 to 5 days will generally be necessary to achieve adequate voiding of the pores.

The sieve may be post-treated, as by steaming, or may be caused to contain other cations either by incorporation during preparation or by subsequent ion-exchange, examples of suitable cations being Ni, Cd, Cu, Zn, Pd, Ca, B and Ti and rare earth metals.

Advantageously, the molecular sieve of the invention has a refined constraint index (as hereinafter defined) greater than 2, and advantageously greater than 10.

The refined constraint index, CI°, is defined in J. A. Martens, M. Tielen, P. A. Jacobs and J. Weitkamp, Zeolites, 1984, p. 98, and P. A. Jacobs & J. A. Martens, Pure and Applied Chem., 1986, Vol. 58, p. 1329, as the ratio of 2-methylnonane to 5-methylnonane produced at 5% conversion in the hydro-isomerization of n-decane.

Examples of molecular sieves having a CI° between 2 and 10 include ZSM-5, 11, 12, 35, 38, 48, and 57, SAPO-11, MCM-22 and erionite, those having a CI° between 5 and 10 presently being preferred. Examples of molecular sieves having a CI° greater than 10, and accordingly most preferred, include ZSM-22, ZSM-23, and certain ferrierites.

It is within the scope of the oligomerization process of the invention to employ mixtures containing two or more molecular sieves.

The molecular sieve or zeolite catalyst is advantageously ZSM-22, described in U.S. Pat. No. 4556477 and in WO 93/25475, the disclosures of which are incorporated herein by reference.

A molecular sieve crystallite size advantageously up to 5 $\mu$m, preferably within the range of from 0.05 to 5 $\mu$m, more especially from 0.05 to 2 $\mu$m, and most preferably from 0.1 to 1.0 $\mu$m, may be employed.

The proportion by weight represented by the surface layer, based on the total weight of the molecular sieve of the invention, may, for example, be within the range of 5% to 20%, conveniently from 8% to 15%, after calcination.

The molecular sieve may be used in the form of granules, powder or other shaped form, e.g., an extrudate. The extrudate advantageously contains the molecular sieve, and a binder, for example alumina, silica, an aluminosilicate, or clay, advantageously in a proportion of from 10:90 to 90:10, preferably 20:80 to 80:20, by weight of sieve to binder. The sieve and binder may be composited by, for example, intimately mixing them together in the presence of water, and extruding or otherwise shaping, e.g., by pelletizing.

The feed olefin advantageously contains from 2 to 12 carbon atoms, and preferably from 2 to 6 carbon atoms; more preferably, the olefin feed advantageously contains propene, butenes and/or pentenes.

Reaction conditions for the oligomerization process of the invention may be, with the exception of the use of the novel catalyst, in accordance with conditions operative for prior art processes oligomerizing the same olefin.

The olefin may, for example, be fed to the catalyst in admixture with an inert diluent, e.g., a saturated hydrocarbon, in the liquid or, preferably, the gaseous, phase. For a feed comprising propene, a suitable diluent is propane, advantageously in proportions of propene:propane from 90:10 to 10:90, preferably from 10:90 to 60:40, especially about 50:50 by weight. Correspondingly, for a butene feed, a suitable diluent is butane, advantageously in proportions from 90:10 to 10:90, preferably from 75:25 to 50:50, especially about 2:1, by weight olefin: saturate. The feed is advantageously hydrated; preferably it contains from 0.05% to 2% by weight water. The desired proportion of water may be incorporated by saturating the feed at an appropriate temperature, e.g., from 25 to 60° C., or by injecting water through a pump.

The oligomerization may take place at a temperature advantageously in the range of from 160° C. to 300° C., preferably from 170° C. to 260° C., and most preferably from 180° C. to 260° C., at a pressure advantageously in the range of from 5 to 10 MPa, preferably from 6 to 8 MPa, and at an olefin hourly space velocity advantageously in the range 0.1 to 20, preferably from 0.5 to 10, and most preferably 0.75 to 3.5, whsv.

In olefin oligomerizations employing a normal prior art catalyst, e.g., ZSM-22, it was found that with a decrease in conversion rate, selectivity to dimer, e.g., from butene to octene, increased but the degree of branching increased also. Using the catalyst of the present invention, however, it has surprisingly been found that, at lower conversion rates, the selectivity to dimer is retained and is accompanied by a decrease in the degree of branching. Accordingly, oligomerization may be carried out at a lower conversion rate, unreacted monomer separated from oligomer, and recycled, resulting in a high dimer selectivity without loss of linearity in the product.

Further, the catalyst of the present invention has the additional advantage over the bulky-amine treated material of the prior art that it may readily be regenerated, as by calcining, without requiring a subsequent amine treatment. The catalyst of the present invention will moreover not differ on regeneration in its ability to oligomerize olefins to a less highly branched product from the catalyst of the invention as originally prepared.

The following examples, in which parts and percentages are by weight unless otherwise stated, illustrate the invention:

EXAMPLE 1 TO 3

Preparation of Catalyst

EXAMPLE 1

Preparation of synthesis mixture:

| Solution A: | |
| --- | --- |
| COMPONENT | PARTS |
| $H_2O$ | 229.64 |
| $Al_2(SO_4)_3 \cdot 18H_2O$ | 0.6538 |
| NaOH (98.4%) | 2.11 |
| 1,6-diaminohexane | 12.85 |

The ingredients were dissolved in the water in the order shown.

| Solution B: | |
| --- | --- |
| COMPONENT | PARTS |
| Ludox AS-40 (Colloidal Silica) | 54.81 |

Solutions A and B were mixed for about 3 minutes, producing a smooth whitish gel (synthesis mixture).

| Mixture C: | |
|---|---|
| COMPONENT | PARTS |
| ZSM-22 ($H_2O$) content 1.18%), $SiO_2/Al_2O_3$ molar ratio 73:1 | 50.00 |
| $H_2O$ | 50.09 |

Particle size of ZSM-22 $\leq 1$ μm.

The components of Mixture C were mixed for 5 minutes, producing a very viscous paste. 72.54 parts of the synthesis mixture (Solutions A & B) were added and mixed for 15 minutes. An easily pourable and homogenous mass was obtained.

The molar composition of the final synthesis mixture (excluding the crystals) was:

$$26.4\ Na_2O/112.6\ R/Al_2O_3/372\ SiO_2/26580\ H_2O$$

where R is 1,6-diaminohexane.

The mixture contained 28.7% preformed ZSM-22 crystals.

80.87 parts of the synthesis mixture were transferred to a stainless steel autoclave and heated to 160° C. over a period of 2 hours, and kept at this temperature for 48 hours.

The product was filtered and washed three times with 500 parts water to pH 9.4 and subsequently dried at 125° C.; 25.88 parts of dried product were recovered. The product after drying had an intense yellowish appearance, indicating that the core crystals were covered with a silica-rich ZSM-22 outer layer or shell. The weight ratio of the shell to core was calculated as follows: Parts of synthesis mixture x Fraction preformed crystals

| | |
|---|---|
| (80.88 × 0.287) | 23.21 |
| Parts of Dried Product | 25.88 |
| Gain | 2.67 |
| Ratio shell/uncalcined core | 2.67/23.21, i.e., 0.12 |

On the assumption that on calcination there is a shell weight loss of about 12%, the expected weight ratio of calcined shell to core is about 0.10:1.

X-ray diffraction (XRD) on the dried product showed a structure of ZSM-22 very slightly contaminated with crystobalite.

EXAMPLE 2

Following the procedure of Example 1 a final synthesis mixture of molar composition $$53.0\ Na_2O/226\ R/Al_2O_3/746\ SiO_2/61045\ H_2O$$

where R is 1,6-diaminohexane, was obtained, containing 29.32% preformed ZSM-22 crystals.

111.24 parts of the crystallite-containing synthesis mixture were transferred to a stainless steel autoclave, which was placed in an oven at room temperature. The oven was heated to 158° C. over a period of 2 hours and maintained at that temperature for 24 hours.

The resulting crystalline product was repeatedly washed with water and dried at 125° C. for 40 hours. 35.8 parts of dry product were recovered. By a calculation as described in Example 1, the weight ratio of uncalcined shell:core was found to be 0.10:1 and the expected calcined shell:core ratio was about 0.09:1. XRD showed a pure crystalline ZSM-22 structure.

EXAMPLE 3

Preparation of synthesis mixture:

| Solution A: | |
|---|---|
| COMPONENT | PARTS |
| $Al_2(SO_4)_3$ $18H_2O$ | 0.2193 |
| NaOH (98.4%) | 2.10 |
| 1,6-diaminohexane | 12.87 |
| $H_2O$ | 175.00 |

The first three components were dissolved in the order shown in the 175 parts of water. 54.82 parts of colloidal silica (Lddox AS40) Solution B were placed in a mixer, solution A was poured over the mixer contents, and the vessel in which solution A was prepared was rinsed with 54.67 parts water, the rinse water then being poured into the mixer. The contents were then stirred for 3 minutes to provide Mixture C. To 40.46 parts of water were added 44.13 parts of Mixture C, the diluted material then being mixed with 35.02 parts of ZSM-22 crystals. After mixing for 5 minutes a viscous but pourable mass D resulted, with a molar composition of:

$$78.9\ Na_2O/336\ R/Al_2O_3/1112\ SiO_2/85320\ H_2O$$

R being 1,6-diaminohexane; with 29.0% dry weight content of ZSM-22 seeds.

110.05 parts of the mass D were transferred to a stainless steel autoclave, which was placed in an oven at room temperature. The oven was then heated to 150° C. over 3 hours and maintained at that temperature for 24 hours. After the separated crystalline product was washed three times to reach a pH (last wash water) of 9.4, it was dried overnight at 120° C., yielding 35.75 parts of dried product. Calculation as described in Example 1 showed a weight ratio of uncalcined shell:core of 0.12:1, and a predicted calcined shell:core of 0.10:1.

In each of Examples 1 to 3, the product was cation exchanged with a 0.5N $NH_4Cl$ solution, washed, and calcined at 400° C. for 16 hours.

EXAMPLE 4 AND 5 AND COMPARATIVE EXAMPLES A, B AND C

Olefin Olicomerization

The following examples were carried out to illustrate the effectiveness of catalysts produced according to the invention in oligomerization of an olefin. In each case, the feed was a mixed butene feed, diluted with butanes, in proportions of approximately 65% olefins and 35% saturates, saturated with water vapour at 40° C. Reactor temperature was maintained in the region of 205 to 235° C., increasing in each case with the number of days on stream. The reactor pressure was maintained at about 7 MPa.

Prior art catalysts used were (a) the ZSM-22 catalyst employed as core crystals in Examples 1 to 3 above (termed "Parent" in Tables 1 and 2 below), and (b) collidine treated ZSM-22; both catalysts (a) and (b) were formed into extrudates of 5 mm diameter; the catalysts according to the invention and catalyst (a) were used as powders. Table 1 shows the catalytic activity in terms of butene conversion at 205° C., 7 MPa and weight hourly space velocity of 1.3 g olefin/g catalyst/hour.

TABLE 1

| Ex. No. | Catalyst | Conversion, % |
|---|---|---|
| Comp. A | (a) Parent, powder | 97.0 |
| Comp. B | (a) Parent, extrudate | 80.3 |
| Comp. C | (b) Collidine-Treated, extrudate | 8.1 |
| 4 | Example 1, powder | 91.3 |
| 5 | Example 2, powder | 84.9 |

EXAMPLES 6 to 13 AND COMPARATIVE EXAMPLES D to H

In these Examples, the catalysts of Examples 1 and 2 and of Comparison Examples B and C were used in butene dimerization and the degree of branching of the resulting octenes was compared. The feed and conditions used were as described above with reference to Examples 4 and 5 above, but feed rates and hence space velocities were varied to give different conversion rates. The results are summarized in Table 2 below.

TABLE 2

| Example No. | Catalyst Example | Butene Conversion (%) | Octene Isomers (%) | | | Average | |
|---|---|---|---|---|---|---|---|
| | | | Linear | Mono Branched | Di Branched | Tri Branched | Branching Degree | Selectivity to dimer (%) |
| Comp. D | Comp. B | 74.8 | 4.2 | 40.6 | 50.2 | 5.0 | 1.56 | 49.5 |
| Comp. E | Comp. B | 84.6 | 3.9 | 39.3 | 52.3 | 4.5 | 1.57 | 48.4 |
| Comp. F | Comp. B | 90.2 | 4.3 | 42.2 | 49.8 | 3.7 | 1.53 | 45.0 |
| Comp. G | Comp. B | 96.1 | 5.8 | 47.4 | 44.9 | 2.0 | 1.43 | 31.7 |
| Comp. H | Comp. C | 73.5 | 8.4 | 66.4 | 23.4 | 0.8 | 1.18 | 58.2 |
| 7 | 1 | 73.9 | 6.1 | 56.3 | 35.1 | 2.5 | 1.34 | 58.2 |
| 8 | 1 | 79.5 | 5.6 | 54.6 | 37.2 | 2.5 | 1.37 | 57.8 |
| 9 | 1 | 91.3 | 4.2 | 45.2 | 47.0 | 3.5 | 1.50 | 48.5 |
| 10 | 1 | 93.4 | 4.7 | 47.1 | 46.0 | 2.2 | 1.46 | 46.1 |
| 11 | 2 | 72.7 | 5.5 | 58.1 | 33.1 | 3.3 | 1.34 | 56.9 |
| 12 | 2 | 81.1 | 5.5 | 56.0 | 35.9 | 2.7 | 1.36 | 61.1 |
| 13 | 2 | 91.5 | 5.4 | 52.2 | 40.5 | 1.9 | 1.39 | 56.5 |
| 14 | 2 | 95.0 | 6.8 | 63.4 | 27.8 | 1.9 | 1.25 | 47.3 |

What is claimed is:

1. A particulate molecular sieve, each particle of the molecular sieve comprising a core having deposited thereon a surface layer, the core comprising a zeolite containing silicon and at least one element selected from the group consisting of gallium and iron, and the surface layer comprising a zeolite containing silicon and aluminum, the zeolite of the surface layer being of the samie crystalline structure as the core and having a silicon:aluminum ratio that is higher than the ratio of silicon:selected element of the core.

2. The particulate molecular sieve of claim 1, wherein the sihicon:selected element ratio of the core is no greater than 120:1.

3. The particulate molecular sieve of claim 1, wherein the silicon:aluminum ratio in the surface layer is at least 150:1.

4. The particulate molecular sieve of claim 1, wherein the molecular sieve has a CI° of at least 2.

5. The particulate molecular sieve of claim 4, wherein said zeolite containing silicon and aluminum is selected from the group consisting of ZSM-5, ZSM-11 and ZSM-22.

6. The particulate molecular sieve of claim 1, wherein the selected element is gallium and said zeolite containing silicon and aluminum is selected from the group consisting of ZSM-5 and ZSM-11.

7. The particulate molecular sieve of claim 1, wherein the proportion by weight of the crystallite represented by the surface layer is in the range of from about 2% to about 20%.

8. The particulate molecular sieve of claim 1, wherein the crystallite represented by the surface layer has a size in the range of from about 0.1 to about 1.0 um.

9. A process for the oligomerization of an olefin, which comprises contacting under oligomerization conditions a feed comprising at least one olefin with an olefin oligomerization catalyst comprising a particulate molecular sieve, each particle of the molecular sieve comprising a core having deposited thereon a surface layer, the core comprising a zeolite containing silicon and at least one element selected from the group consisting of gallium and iron, and the surface layer comprising a zeolite containing silicon and at least one element selected from the group consisting of gallium and iron, the zeolite of the surface layer being of the same crystalline structure as the core and having a higher silicon:selected element ratio than that of the core.

10. The process of claim 9, wherein the olefin contains from about 2 to about 12 carbon atoms.

11. The process of claim 9, wherein said process is carried out at a temperature within the range of from about 160° C. to about 300° C.

12. The process of claim 9, the oligomers produced by said process have a reduced degree of branching.

13. A process for the manufacture of a particulate molecular sieve, which comprises heating an aqueous synthesis mixture comprising a source of silicon, aluminum, a source of monovalent inorganic cations, and optionally an organic structure directing agent, the synthesis mixture having dispersed therein crystals of a molecular sieve containing silicon and an element selected from the group consisting of gallium and iron, the molar ratio of silicon to selected element in the crystals being lower than the molar ratio of silicon to aluminum in their respective sources in the synthesis mixture, to cause crystallization of a molecular sieve layer from the synthesis mixture onto the surfaces of the crystals.

14. A process for the oligomerization of an olefin, which comprises contacting under oligomerization conditions a feed comprising at least one olefin with an olefin oligomerization catalyst comprising a particulate molecular sieve, each particle of the molecular sieve comprising a core having deposited thereon a surface layer, the core comprising a zeolite containing silicon and at least one element selected from the group consisting of gallium and iron, and the surface layer comprising a zeolite containing silicon and aluminum, the zeolite of the surface layer being of the same crystalline structure as the core and having a silicon:aluminum ratio that is higher than the ratio of silicon:selected element of the core.

* * * * *